US010258657B2

(12) United States Patent
Grimaldi et al.

(10) Patent No.: US 10,258,657 B2
(45) Date of Patent: Apr. 16, 2019

(54) THERAPEUTIC AND NUTRITIONAL COMPOSITIONS FOR FUNCTIONAL GASTROINTESTINAL DISORDERS

(71) Applicant: ALFA WASSERMANN S.p.A., Alanno (PE) (IT)

(72) Inventors: Maria Grimaldi, Bologna (IT); Maria Vittoria Fogli, Bologna (IT); Giuseppe Claudio Viscomi, Bologna (IT)

(73) Assignee: ALFASIGMA S.P.A., Bologna (IT)

( * ) Notice: Subject to any disclaimer, the term of this patent is extended or adjusted under 35 U.S.C. 154(b) by 0 days.

(21) Appl. No.: 15/509,002

(22) PCT Filed: Sep. 9, 2015

(86) PCT No.: PCT/EP2015/070579
§ 371 (c)(1),
(2) Date: Mar. 7, 2017

(87) PCT Pub. No.: WO2016/041826
PCT Pub. Date: Mar. 24, 2016

(65) Prior Publication Data
US 2017/0258860 A1    Sep. 14, 2017

(30) Foreign Application Priority Data
Sep. 16, 2014  (EP) .................................. 14185003

(51) Int. Cl.
| | |
|---|---|
| *A23L 2/52* | (2006.01) |
| *A61K 9/48* | (2006.01) |
| *A23L 33/00* | (2016.01) |
| *A61K 31/12* | (2006.01) |
| *A23L 33/105* | (2016.01) |
| *A61K 36/235* | (2006.01) |
| *A61K 36/9066* | (2006.01) |

(52) U.S. Cl.
CPC .............. *A61K 36/235* (2013.01); *A23L 2/52* (2013.01); *A23L 33/105* (2016.08); *A23L 33/30* (2016.08); *A61K 9/4825* (2013.01); *A61K 9/4858* (2013.01); *A61K 31/12* (2013.01); *A61K 36/9066* (2013.01); *A23V 2002/00* (2013.01)

(58) Field of Classification Search
CPC ............ A23V 2002/00; A23V 2200/32; A23V 2250/21; A23V 2250/2112; A23L 33/105; A23L 33/30; A61K 36/235; A61K 36/9066; A61K 9/4825; A61K 9/4858; A61K 45/06; A61K 9/4808; A61K 9/4833; A23P 10/30; A61J 3/074
See application file for complete search history.

(56) References Cited

U.S. PATENT DOCUMENTS

2004/0258775 A1  12/2004  Patel

FOREIGN PATENT DOCUMENTS

| CN | 101780252 B | 11/2011 | |
|---|---|---|---|
| CN | 103301404 A | 9/2013 | |
| FR | 2876250 B1 | 10/2008 | |
| WO | 2008074080 A1 | 6/2008 | |
| WO | 2010106191 A1 | 9/2010 | |
| WO | WO 2010106191 A1 * | 9/2010 | ........... A61K 9/4858 |
| WO | WO 2013118099 A1 * | 8/2013 | ............. A61K 36/28 |

OTHER PUBLICATIONS

Akiho (World Journal of Gastrointestinal Pathophysiology, 2010, vol. 1, pp. 97-105) (Year: 2010).*
Anand et al., "Bioavailability of curcumin: problems and promises.", Mol Pharm. Nov.-Dec. 2007;4(6):807-18. Epub Nov. 14, 2007.
Bundy et al, "Turmeric extract may improve irritable bowel syndrome symptomology in otherwise healthy adults: a pilot study.", J Altern Complement Med. Dec. 2004:10(6):1015-8.
Francis et al, "The irritable bowel severity scoring system: a simple method of monitoring irritable bowel syndrome and its progress.", Aliment Pharmacol Ther. Apr. 1997:11(2):395-402.
Gupta et al, "Therapeutic roles of curcumin: lessons learned from clinical trials", AAPS J. Jan. 2013; 15(1):195-218.
Irving et al, "Curcumin: the potential for efficacy in gastrointestinal diseases", Best Pract Res Clin Gastroenterol. Aug. 2011:25(4-5):519-34.
Lee et al., "Irritable bowel syndrome: emerging paradigm in pathophysiology", World J Gastroenterol. Mar. 14, 2014;20(10):2456-69.
Mishra et al., "Functional natural ingredients for "irritable bowel syndrome"", International Journal of bioassays, vol. 2(1), (2013): 338-340.
Portincasa, et al., "Curcumin and Fennel Essential Oil Improve Symptoms and Quality of Life in Patients with Irritable Bowel Syndrome.", J Gastrointestin Liver Dis. Jun. 2016:25(2)151-7.
Rajasekaran SA, "Therapeutic potential of curcumin in gastrointestinal diseases", World J Gastrointest Pathophysiol. 2011 Feb. 2015;2(1):1-14.
Sasha L., "Irritable bowel syndrome: Pathogenesis, diagnosis, treatment, and evidence-based medicine", World J Gastroenterol. Jun. 14, 2014; 20(22): 6759-6773.
Shimouchi et al, "Effect of dietary turmeric on breath hydrogen." Dig Dis Sci. Aug. 2009; 54(8):1725-9. Epub Nov. 26, 2008.
Baidyanath M., et al., "Functional natural ingredients for irritable bowel syndrome", International Journal of Bioassays, Jan. 1, 2013, pp. 338-340.
Farooq A., et al., "Antioxidant and antimicrobial activities of essential oil and extracts of fennel (*Foeniculum vulgare* Mill.) seeds from Pakistan", Flavour and Fragrance Journal, vol. 24, No. 4, Jul. 1, 2009, pp. 170-176.
International Search Report of PCT/EP2015/070579 dated Dec. 10, 2015.
Jurenka, J., "Curcumin, a major constituent of Curcuma longa: a review of preclinical and clinical research," Alternative Medicine Review vol. 14, No. 2, Jun. 1, 2009, pp. 141-153.

(Continued)

*Primary Examiner* — Mark V Stevens
(74) *Attorney, Agent, or Firm* — Silvia Salvadori, P.C.; Silvia Salvadori

(57) ABSTRACT

The present invention relates to nutritional compositions containing balanced amount of substance having anti-inflammatory activity, as curcumin, and substance having carminative and spasmolytic activities, as essential plant oil, for the treatment and/or prevention of functional gastrointestinal disorders.

11 Claims, No Drawings

(56) References Cited

OTHER PUBLICATIONS

Werayut, P., et al., "Quantitative analysis of curcumin, demethoxycurcumin and bisdemethoxycurcumin extract from Curcuma longa in Thailand by TLC-Densitometry", Mahidol University Journal of Pharmaceutical Sciences, Jan. 1, 2005, pp. 23-30.
Written Opinion of PCT/EP2015/070579 dated Dec. 10, 2015.

* cited by examiner

THERAPEUTIC AND NUTRITIONAL COMPOSITIONS FOR FUNCTIONAL GASTROINTESTINAL DISORDERS

This application is a U.S. national stage of PCT/EP2015/070579 filed on 9 Sep. 2015, which claims priority to and the benefit of European Patent Application No. 14185003.2 filed on 16 Sep. 2014, the contents of which are incorporated herein by reference in their entireties.

STATE OF THE ART

Functional gastrointestinal disorders (FGID) are the most common GI disorders in the population. The term "functional" is generally applied to disorders where the body's normal activities in terms of movement of the intestines, the sensitivity of the nerves of the intestines, or the way in which the brain controls some of these functions is impaired.

Functional gastrointestinal disorders include a number of separate idiopathic disorders which affect different parts of the gastrointestinal tract.

Irritable bowel syndrome (IBS) is the most common gastrointestinal disorder; it is a functional disorder characterized by symptom including abdominal pain, bloating, altered bowel habit and change in stool frequency. There is also evidence that health related quality of life is significantly reduced in patient suffering from IBS compared to healthy control.

These symptoms cannot be explained by structural abnormalities and there is no specific laboratory test or biomarker for IBS diagnosis. Therefore, IBS is classified as a functional disorder with diagnosis dependent on the clinical history taking about manifested symptoms and physical examination.

Although a great deal of research has been carried out in this area, the pathophysiology of IBS is complex and not completely understood. Multiple factors are thought to contribute to the symptoms in IBS patients such as altered gastrointestinal motility, visceral hyper sensibility, and brain-gut interaction. New areas of research include inflammation, post-infectious low-grade inflammation, genetic and immunologic factors, an altered microbiota, dietary factors, and enter-endocrine cells. These emerging studies have not shown consistent results, provoking controversy in the IBS field. However, certain lines of evidence suggest that these mechanisms are important at least a subset of IBS patients, confirming that IBS symptoms cannot be explained by a single etiological mechanism.

Irritable bowel syndrome is usually evaluated and managed with questionnaires administered to patients to evaluate the efficacy of IBS treatment. The questionnaires include many severity symptomatology, score which consider different facets of IBS such as primary symptomatology, non-colonic features, quality of life and psychological factors, which can change independently of each other.

A number of mono-target "smart" drugs have emerged over the past decade, however some diseases as IBS, caused by perturbation of multiple signaling pathways, attacking only one of these multiple pathways, often are highly unlikely to be effective. In addition mono-target "smart" drugs can produce adverse effects to different organs and for that not well accepted by the patients.

Gupta S. et al in AAPS Journal 15, 195, 2013 describes the use of curcumin in human disease as cholecystis, cancer and diseases connected to an inflammation pathway.

Irvin G. R. B. et al in Best Practice Res Clin Gastroent 25, 519, 2011 describes the use of a natural product as curcumin in gastrointestinal disease, but the efficacious doses have not been determined.

Amand P. et al in Molecular Pharmac 4, 807, 2007 describes that curcumin has varied pharmacological effects including anti-inflammatory, antioxidant, antiproliferative and antiangiogenic activities, but its efficacy is limited by the poor absorption.

Bunty R. et al in J. Alternat Compl Medicine, 10, 105, 2004, states that there is no accepted cure for IBS and phytochemicals in the form of herbal remedies can offer sometime relief. For example, peppermint oil and artichoke leaf extract, have been shown to reduce symptom severity in patients with dyspepsia identified as suffering from IBS. He also reports that Turmeric (*Curcuma longa*) used in Western herbal medicine for conditions as poor digestion, abdominal pain and distension are efficacious in inflammatory diseases and has showed relief in patients suffering from IBS. The patients which received compositions containing 72 mg and 144 mg curcumin for eight weeks showed an improvement in abdominal pain discomfort score, but no difference in the efficacy resulted at different treatment dosage.

US 2004/0258775 describes pharmaceutical composition comprising herbal ingredients such as asafetida, ajwain seed, vidanga, curcumin seed, fenugreek, triphala fennel seed and turmeric, useful in the treatment of headaches, blood constipation, tapeworm, hemorrhoid and stomach acidity. This document does not report the efficacy of this composition in comparison with the known beneficial effect of singular excipients in the different diseases and it does not mention IBS.

CN 103301404A discloses medicine comprising a mixture of at least fifteen herbal species including curcuma aromatic and fennel useful for treating rex rabbit intestinal spasm. This document does not report the absolute amount of the composition and it does not report the efficacy of the composition in human.

Mishra et al. in "Functional natural ingredients for irritable bowel syndrome" discloses the use of natural ingredient to treat gastrointestinal conditions used in traditional medicinal system in various regions like China, Tibet and India. Among the list of herbal ingredient this document reports curcuma and fennel, but it does give any information on the efficacious dosage of the cited ingredient and the preferred ingredient for the treatment of IBS.

CN 101780252A discloses a traditional Chinese medicine comprising at least twenty herbal ingredients useful for abdominal distension. Among the list of natural ingredients this document reports turmeric and fennel, but no mention is done about the efficacious amount of these components for the treatment of IBS or relieve of symptom associated with IBS.

FR 2876250 discloses a dietetic compound useful to restore the natural cycles hormones serotonin which control the fluctuations of weight control of satiety in the body but it does not make any mention on the symptoms connected to IBS.

Curcumin is characterized by having a low solubility in aqueous solution and thereof its bioavailability is low, independently by the administered amount. The bioavailability of curcumin can be increased in the presence of substance able to do that, but starting from the prior art there is no information on the efficacious dosage and period of treatment in the IBS without any side effect.

WO 2010/106191 describes the use of curcumin in inflammatory disease, in particular osteoartrithis and it suggests that the addition of polysorbate increases the solubility of the curcumin. However these compositions are referred to the treatment of osteoarthritis and no mention is done to the efficacious dosage, period of treatment and tolerability of curcumin.

Starting from the prior art, there is a need to have new efficacious compositions without any side effect, well tolerated by the patients for the treatment of functional gastrointestinal disorder. In particular the composition containing balanced amount of curcumin and fennel oil is useful for the treatment of IBS.

SUMMARY OF THE INVENTION

The present invention relates to nutritional compositions containing balanced amount of substance having anti-inflammatory activity such as curcumin and substance having carminative and spasmolytic activities activity, such as one or more essential plant oils, for the treatment and/or prevention of functional gastrointestinal disorder.

In another aspect the invention relates to nutritional compositions for the treatment Irritable Bowel Syndrome (IBS).

In another aspect the invention relates to nutritional compositions for the treatment Irritable Bowel Syndrome with mild to moderate symptoms.

The compositions of the invention comprise curcumin in an amount from 10 to 200 mg and a plant essential oil in an amount from 5 to 50 mg. A preferred composition comprises curcumin in an amount from 20 to 100 mg, more preferably from 20 to 50 mg and plant essential oil in an amount from 15 to 35 mg. Curcumin may be in form of powder or essential extracted oil.

Fennel essential oil is the preferred plant essential oil to be contained in the nutritional compositions for use in the treatment of intestinal disorders, in particular in IBS treatment.

The compositions are in a form to be orally administered and gelatin capsules are the preferred forms, administering one, two, three or four gelatin capsules per day.

The compositions can be administered one, two, three or four times a day.

The compositions containing curcumin and fennel essential oil are useful in the treatment and prevention of IBS at a daily dosage from 10 mg to 3200 mg of curcumin, preferably from 20 to1600 mg, more preferably from 40 to 800 mg and fennel oil at a daily dosage from 5 to 800 mg, preferably from 15 to 560 mg and more preferably from 15 to 400 mg.

The compositions of the invention are prepared with a method which comprises the steps of mixing curcumin powder or extracted oil with citric acid and fennel oil for obtaining a homogeneous mixture; adding polysorbate 80 and uploading homogeneous mixture into gelatin capsules.

The compositions of the invention are efficacious in the treatment and prevention of functional gastrointestinal disorder, in particular in the treatment of IBS.

In a particular aspect the compositions of the invention are efficacious in the treatment of IBS with mild to moderate symptom for a treatment period of at least 10 days preferably at least 20 days.

In a particular aspect the compositions of the invention are efficacious in the treatment of IBS with mild to moderate symptom, reducing the IBS severity score in respect to the begin of the treatment, for a treatment period of at least ten days.

The nutritional compositions of the invention are safety and well tolerated by the patient and they can be administered for the life time.

The composition of the invention can be administered with concomitant therapy, without any collateral effect or reduction of the efficacy of the curcumin and fennel oil.

DESCRIPTION

The present invention relates to nutritional compositions containing balanced amount of substance having anti-inflammatory activity such as curcumin and substance having spasmolytic and carminative activity such as essential plant oil, for the treatment and/or prevention of functional gastrointestinal disorder.

In a particular aspect the invention relates to the use of the composition comprising balanced amount of substance having anti-inflammatory activity such as curcumin and substance having spasmolytic and carminative activity such as essential plant oil for the treatment of Irritable bowel syndrome (IBS).

The object is achieved according to the present invention with a composition of substances already known in themselves, but combined in a new and opportunely balanced way to be given in the diet of subjects having the aforesaid needs.

The nutritional compositions are specified in claim 1 and other characteristics are specified in depending claims. The compositions of the invention beside being easily usable, have the basic advantage of providing the consumer with an aggregate of substance each having a well determined activity and being mutually dosed in a optional way. The nutritional compositions contain a determined and opportunely coordinated amounts of two substances, wherein one having anti-inflammatory and antioxidant activity and a second one having property to relax smooth muscle of the intestine.

The first substance having anti-inflammatory and antioxidant activity, opportunely selected for the nutritional compositions according to the invention is curcumin, a natural substance derived from the rhizome of the herb *Curcuma longa* which has a wide spectrum of biological and pharmacological activities. Chemically, curcumin is a bis-$\alpha$, $\beta$-unsatured $\beta$- diketone (commonly called diferuloymethane), which exhibit keto-enoltautomerism having a predominant keto form I acid and neutral solution and stable enol form in alkaline medium. Curcumin has demonstrated anti-inflammatory activity in vitro and it is effective in reducing mucosal injuries in an animal model of colitis by modulating I-kappa.

B kinase activity, inhibiting NF-KB and the expression and release of pro-inflammatory cytokines (TNF-alfa, IL 1$\beta$, IL-6). Traditionally, turmeric has been used for many aliments and curcumin is the principal curcuminoid of the popular Indian curry spice turmeric. Curcumin at neutral and basic pH is rapidly degraded in vitro and when eaten, little, or nothing curcumin is absorbed and it undergoes rapid intestinal metabolism and its intestinal absorption is low, precluding reaching blood concentration.

Curcumin in the nutritional compositions of the invention may be in form of powder or extracted oil (Turmeric rhizome extract).

Curcumin is present in the composition of the invention in amounts comprised between 10 and 200 mg, preferably between 20 and 100 mg, and more preferably between 20 and 50 mg according to the intake dose and/or dispensing form.

The second substance of the composition having smasmolytic and carminative activities is fennel essential oil. Fennel essential oil is characterized for containing anethole, a compound with a chemical structure similar to dopamine. It is present in the composition in amount comprised between 5 and 50 mg, preferably between 15 and 35 mg, and more preferably between 15 and 25 mg depending on the intake dose and/or dispensing form.

The compositions also contain a substance having the property to increase the curcumin solubility, such as a polysorbate in an amount between 400 and 700 mg.

The compositions of the invention combine anti-inflammatory and antioxidant properties of curcumin with the property of relaxing intestinal muscle useful for the treatment of IBS. The compositions may also contain antioxidant as Vitamin C and Vitamin E and salts.

Depending on the intake dose and/or dispensing form, the dietary composition according to the present invention can also comprise excipients, fragrances and other substances having a known activity for the desired purpose and their amount are to be selected each time depending on the dosage and on the dispensing way of the dietary composition according to the present invention.

It has been found and it is object of the invention that the nutritional compositions of the invention, which combine the actions of curcumin and fennel oil are efficacious in the treatment of functional gastrointestinal disorders, in particular Irritable Bowel Syndrome (IBS).

In another aspect the compositions of the invention are useful in the treatment of IBS with mild to moderate symptom.

The preparation techniques of the compositions according to the present invention are chosen in function of the dispensing way and other practical consideration.

The nutritional compositions of the invention may be comprised in form of gelatine capsules, soft gel capsules, stick monodose, vials and syrup.

A preferred composition is in form of gelatine capsules for oral administration.

An aspect of the present invention relates to the use in IBS treatment, of compositions for oral administration containing as active ingredients:
curcumin in an amount from 10 to 200 mg, fennel essential oil in an amount from 5 to 50 mg, an emulsifier in an amount from 200 to 700 mg and with pharmaceutically and/or alimentary acceptable excipients.

According to a preferred aspect of the invention the compositions contain:
curcumin in an amount from 20 to 100 mg; fennel essential oil from 15 to 35 mg and a polysorbate from 400 to 700 mg and pharmaceutically and/or alimentary excipients.

According to a more preferred aspect of the invention the compositions contain the components in their respective amounts:
curcumin from 20 to 50 mg; fennel essential oil from 15 to 25 mg; polysorbate-80 from 600 to 700 mg; citric acid from 0.5 to 35 mg and pharmaceutically and/or alimentary excipients.

According to a more preferred aspect of the invention, the composition contains 42 mg curcumin, 600 mg polysorbate-80, 17.5 mg fennel oil and 3.5 mg citric acid in gelatin capsules. The compositions optionally may contain edulcorant, glycerine, colorants, antioxidant salts and water.

The nutritional compositions of the invention in form of gelatine capsules are characterized for having a weight less than 1 gram.

According to another aspect of the invention, is a method for preparing nutritional compositions containing curcumin in an amount from 10 to 200 mg and fennel oil in an amount from 5 to 50 mg, which comprise the step of mixing curcumin powder with citric acid and fennel oil for obtaining an homogeneous mixture; adding polysorbate 80 under stirring and uploading homogeneous mixture into gelatin capsules.

The compositions of the invention may be administered one, two, three or four times a day in one, two, three or four gelatin capsules per day.

The compositions of the invention may be administered with a aqueous solution, beverage or with a solid, or semisolid food.

Another aspect of the invention are kits containing the nutritional composition with curcumin and fennel oil.

The compositions of the invention containing curcumin and plant essential oil, wherein the plant essential oil is fennel oil, are useful in the treatment and prevention of functional gastrointestinal disorder.

In particular, the nutritional compositions are useful in the treatment and/or prevention of IBS. In a more particular aspect the nutritional compositions are useful in the treatment of IBS with mild to moderate symptoms.

The nutritional compositions are efficacious at respectively daily dosage curcumin from 10 to 3200 mg and fennel oil from 5 to 800 mg, in particular curcumin from 20 mg to 1600 and fennel oil from 15 to 560 mg.

In another particular aspect the compositions are efficacious at respectively daily dosage curcumin from 40 to 800 mg and fennel oil from 15 to 400 mg.

In a more particular aspect the nutritional compositions are efficacious in the IBS treatment at daily dosage 168 mg curcumin and 70 mg fennel essential oil.

In another aspect of the invention, the composition can be administered for all the life time for reducing the symptom related to the functional gastrointestinal disorders, in particular IBS with an increase of the quality of life, without any side effects and well tolerated by the patients.

The nutritional compositions are efficacious in the reduction of IBS severity score for a period of treatment at least 10 days, at least 20 days.

Severity score is based on the symptom associated with the IBS, such as abdominal pain, number of days without pain, abdominal distension and bloating, bowl habit and patient's global judgment. The score is calculated by means of a Visual Analogue Scale (VAS). The VAS is long 100 mm, value 0 corresponds to the absence of pain while value 100 corresponds to the high acceptable pain.

The compositions are efficacious in the reduction of IBS severity score for a period of treatment of 30 days.

The bioavailability of nutritional compositions of the invention was evaluated with a pharmacokinetic study in a Phase I study and the results are reported in Example 2, wherein it is shown that the administration of compositions of curcumin and fennel essential oil at daily dosage of curcumin from 10 to 3200 mg provides an anti-inflammatory effect and fennel essential oil at daily dosage from 5 to 800 mg provide topical effect without any toxic affect.

Curcumin and fennel oil were detected in plasma and urine samples over 24 hours; curcumin and its derivative were determined by a validated UHPLC-MS/MS method and trans-anethole of fennel oil by means GC-MS method.

No native curcumin was detected in the plasma; plasma and urine were treated with β-glucuronidase and arylsulfatase and the deconiugated forms of curcumin analyzed after organic solvent extraction. Curcumin was detected as glucuronidase and sulfates of curcumin. First quantifiable curcumin concentrations in plasma were detected in 1 hour; maximum plasmatic concentration ($C_{max}$) is about 100 ng/ml with two capsules and about 300 ng/ml with four capsules administered. $T_{max}$ was about 1 hour in both groups.

The amount of curcumin secreted in urine resulted in the first 4 hours with an amount lower than 60 µper samples in the group which received 2 capsules and lower than 150 µin group which received 4 capsules.

In Phase I clinical study, also hexahydrocurcumin, a metabolite of curcumin, which inhibit COX-2 expression, was detected as glucuronides and sulfates in the plasma samples. First quantifiable hexahydrocurcumin concentrations in plasma were detected in a time of about one hour with $C_{max}$ values of about 10ng/ml with 2 capsules and 20 ng/ml for 4 capsules. The hexahydrocurcumin found in plasma has demonstrated that the amount of the curcumin contained in the present composition of the invention and the daily dosage of the composition is sufficient to provide an anti-inflammatory activity.

No significant trace of trans-anethole was found in plasma and urine samples at demonstration that the fennel oil amount contained in the composition and the daily dosage of the composition exert only topical action.

None of the subjects had adverse event and the composition resulted well tolerated.

The following operative examples describe efficacy of the composition containing curcumin in an amount from 10 to 200 mg and fennel oil in an amount from 5 to 50 mg, in a clinical study in patients with IBS mild to moderate symptom of functional bowel disorder defined by an IBS with severity score between 100 and 300 and abdominal pain score between 30 and 70 on a 100 mm Visual Analogue Scale (VAS).

The score was determined by a validated questionnaire administered which was evaluated at the end of the treatment period wherein symptom improvement and impact of the treatment on quality of life.

The severity of the symptom was evaluated with the IBS-severity score questionnaire which has produced a quantitative score ranging from 1 to 500. When the score is lower than 75 a remission is ascertained.

Scores from 75 to 175 give information on IBS with mild symptom; score from 175 and 300 give information on IBS with moderate symptom and scores higher 300 give information of IBS severe symptoms.

The IBS-Quality of life (QoL) questionnaire incorporates many aspects related to the disease as pain, distension, bowel dysfunction and quality of life/global well-being. The used method is significant and it has a significant difference between controls and patients as a whole (P=0.0001) as well significant differences (P<0.01) between all severity categories. The scoring system applied for evaluating the efficacy of the composition containing the association of curcumin and fennel oil in the IBS treatment with the question and the parameter included, made this method an affordable and reproducible tool.

The nutritional compositions containing the association of curcumin and fennel oil at a respectively daily dosage from 10 to 3200 mg and from 5 to 800 mg is efficacious for decreasing IBS-severity scores higher than 50 points after a period of treatment of at least 10 days compared to baseline value. In a preferred aspect the nutritional compositions decrease IBS severity score when it is administered for a time longer than 20 days and in a more preferred aspect when it is administered for 30 days.

The primary efficacy endpoint (relative decrease of IBS-severity score at the end of treatment) was evaluated after 30 days of treatment and it demonstrated the efficacy of the composition in the reduction of all the symptoms in respect to the baseline.

The secondary efficacy endpoints of the clinical study for efficacy evaluation of the composition containing curcumin at a daily dosage from 10 to 3200 mg and fennel oil daily dosage from 5 to 800 mg were:

decrease of IBS-SS total severity score from baseline after 10 and 20 days of treatment;

evaluation of the patients who responded to the treatment of IBS related disorder with a reduction in IBS-severity score higher than 50 after 30 days of treatment;

decrease of single items of the IBS-severity score questionnaire (abdominal pain, abdominal distension and bloating, bowel habit, patient's global judgment) from baseline, during all treatment period, until the end of treatment;

increase of the number of days without the presence of pain in the last 10 days from baseline during the treatment and at the end of treatment.

The use of the nutritional compositions containing curcumin and fennel oil has demonstrated in a clinical study, statistically significant reduction of abdominal pain and all the symptoms related to IBS. This improvement generated by the use of the compositions was associated with an increase of the quality of life evaluated at the end of the treatment.

IBS total severity score, single quantitative items of IBS-severity score and the number of days without the presence of pain in the last 10 days have been summarized by treatment group and day by means of descriptive statistics. At each post-baseline day, the absolute change from baseline have been summarized by treatment group by means of descriptive statistics and a paired t-test has been performed within each treatment group.

Supportive examples report the efficacious of the composition of the invention in the treatment of functional gastrointestinal disorders such as IBS mild to moderate characterized by severity score from 75 to 300 points.

A mixed model for repeated measures with absolute, or relative changes from has been created for evaluating the efficacy of the compositions containing curcumin and fennel oil and the treated groups were compared. Total Severity Score-IBS, single quantitative items of IBS-severity score and the number of days without the presence of pain in the last ten days have been evaluated by the use of validated questionnaire. A statistical method has been used for the analysis of the data.

The compositions of the invention resulted to be efficacious in the treatment of IBS with mild to moderate symptoms with a reduction in IBS- Total Severity Score higher 50 points in a time less than two months and the decrease of the IBS-SS Total severity score at the primary end-point was significant in respect to the placebo.

The compositions of the invention achieved an higher percentage decrease on the IBS-SS total severity score in respect to the placebo.

The secondary efficacy endpoints at the visit after 10 and 20 days treatment have demonstrated that the compositions of the invention decrease IBS-SS total severity score in a significant mode after a period of time of at least 10 days and in particular about twice in respect to the group treated with placebo.

Clinical study has demonstrated that the compositions containing balanced amount of curcumin and fennel oil are useful in the treatment of IBS reducing in a significant mode absolute and relative abdominal pain, abdominal distension and bloating, bowel habit, increase of the days without the presence s of the pain. The compositions of the present invention also improve all the aspects of the quality of life of the patients with functional gastrointestinal disorder without any adverse events and well accepted by the patients.

EXAMPLE 1

Soft Gelatine Capsules

A proportionally amount of curcumin was mixed with citric acid and polysorbate 80 and the mixture was stirred. Seed fennel oil was added under stirring to the homogeneous mixture. The resulting composition was made of 6% (w/w) curcumin, 0.5% (w/w) citric acid, 2.5% fennel oil completed to 100% (w/w) with polysorbate 80 (88.6% w/w).

The final composition of active ingredients with average fill mass of 700 mg±7.5% was uploaded in gelatin capsules also containing glycerine, Pearlescent pigment red, Pearlescent Pigment Brown, iron oxide, iron oxide black and water.

The final weight of the obtained capsules was 920 mg±8.1%.

The unitary composition of the ingredients in the gelatin capsules is: 42 mg curcumin, 600 mg polysorbate 17.5 mg fennel oil and 3.5 mg citric acid.

A solubility test of the obtained capsules was performed at 37° C. in phosphate buffer at neutral pH value and the solubilized amount of curcumin after 1 hour resulted in an amount of 50% in respect to the initial dose.

The obtained soft gelatin capsules were packaged in paperboard boxes containing a food grade plastic bag.

Placebo capsules were prepared in the same mode without curcumin and fennel oil.

EXAMPLE 2

Pharmacokinetic of the Composition Containing Curcumin and Fennel Essential Oil

A phase I cross-over pharmacokinetic study was carried out on twelve healthy subjects who received 2 or 4 capsules prepared according to Example 1, in single dose at 14 days interval period.

Blood samples were taken at time 0, 1, 2, 4, 8 and 24 hours. Curcumin and derivatives were determined by a validated UHPLC-MS/MS method and trans-anethol was analyzed by means of a GC-MS method.

No native curcumin was detected in plasma, at any dosage or in any individual.

a. Curcumin Determination

Curcumin concentrations were evaluated after enzymatic hydrolysis of samples. Plasma and urine samples were then treated with β3-glucuronidase and arylsulfatase for 3 hours at 37° C. and deconiugated forms of curcumin were then extracted by organic solvents and quantified using the same validated UPLC-MS/MS analytical method.

First quantifiable curcumin concentrations in plasma were detected in 1 hour by the first administration.

Table 1 reports the values of total curcumin plasmatic concentration ($C_{max}$, $AUC_{0-t}$, $T_{max}$, $T_{1/2}$).

TABLE 1

| Dosage | $C_{max}$ (ng/ml) | $AUC_{0-t}$ (ng · h/ml) | $AUC_{0-inf}$ (ng · h/ml) | $T_{max}$ (hour) | $T_{1/2}$ (hour) |
|---|---|---|---|---|---|
| 2 capsules Example 1 | 108.3 ± 64.0 | 380.3 ± 299.6 | 388.8 ± 245.9 | 1.08 ± 0.29 | 3.31 ± 1.66 |
| 4 capsules Example 1 | 286.6 ± 211.4 | 934.6 ± 608.9 | 944.3 ± 619.2 | 1.00 ± 0.0 | 2.88 ± 0.97 |

The limit of quantification of the method (LLOQ) was equals to 5 ng/ml and the limit of detection (LOD) was estimated to be around 1.5 ng/ml.

The curcumin amount secreted in urine resulted in the first 4 hours and Table 2 reports the curcumin concentration in urine during 24 hours.

TABLE 2

| | Curcumin concentration in urine (µg/ml) | | | |
|---|---|---|---|---|
| Dosage | 0 hours | 4 hours | 8 hours | 24 hours |
| 2 capsules Example 1 | 0.00 ± 0.0 | 0.10 ± 0.08 | 0.03 ± 0.02 | 0.01 ± 0.01 |
| 4 capsules Example 1 | 0.00 ± 0.0 | 0.24 ± 0.19 | 0.10 ± 0.09 | 0.03 ± 0.03 | b. Hexahydrocurcumin Determination

Hexahydrocurcumin was detected as glucoronides and sulfates of hexahydrocurcumin in plasma samples, after treatment with β-glucoronidase and arylsulfatase for 3 hours at 37° C. and the deconjugated forms of hexahydrocurcumin were extracted with organic solvent and quantified by UPLC-MS/MS.

Table 3 reports the PK parameters for hexahydrocurcumin.

TABLE 3

| Dosage | $C_{max}$ (ng/ml) | $AUC_{0-t}$ (ng · h/ml) | $AUC_{0-inf}$ (ng · h/ml) | $T_{max}$ (hour) | $T_{1/2}$ (hour) |
|---|---|---|---|---|---|
| 2 capsules Example 1 | 9.16 ± 5.22 | 61.97 ± 25.07 | 72.31 ± 37.79 | 1.33 ± 0.49 | 6.96 ± 7.83 |
| 4 capsules Example 1 | 18.6.6 ± 7.99 | 117.47 ± 48.12 | 124.35 ± 52.80 | 1.50 ± 0.52 | 5.21 ± 2.032 | c. Trans-anethole Determination

No significant trace of trans-anethole was observed in plasma and urine after; all the concentration in samples were below Limit of Detection (LOD), estimated around 30ng/ml.

EXAMPLE 3

Efficacy of the Composition Containing Curcumin and Fennel Essential Oil in the IBS Treatment 121 Adults patients of both sex, with age comprised between 18 and 60 years old, with specific functional gastrointestinal symptoms, six months before the enrollment in the clinical study, were randomized at baseline visit to receive 2 capsules prepared according to Example 1 or placebo, BID for 30 days under fasting conditions.

At the baseline visit, the patients had an Irritable Bowel Syndrome Symptom Severity Score (IBS-SS) between 100 and 300 points; abdominal pain/discomfort between 30 and 70 points, measured on a 100 mm visual analogue scale (VAS) for at least 3 days in the 10 days preceding the enrolment, and the presence of at least one of the following symptoms: abdominal distension and dissatisfaction with bowel habits.

Patients were evaluated at baseline, before the treatment (day 0) and at the visit after 10 days, 20 days and 30 days at the end of treatment and at the patients completed the IBS-SS questionnaire.

The IBS-SS questionnaire produced a quantitative score ranging from 0 to 500 for estimation of symptom severity: scores lower than 75 represent remission; scores between 75 and 175 represent mild symptoms; scores between 175 and 300 represent moderate symptoms and scores higher than 300 represent severe symptoms.

The IBS Quality of Life (QoL) questionnaire was used as a self-reported measure to assess the impact of the treatment on quality of life and completed at baseline and at the end of treatment.

The primary endpoint was the relative decrease of IBS-severity score at final visit after 30 days treatment time in respect to the baseline.

Secondary endpoints were the evaluation at the visits after 10 and 20 days treatment time in respect to the baseline by the evaluation of the following symptoms: abdominal pain score; relative decrease of abdominal pain score; absolute change of bowel distension and dissatisfaction with bowel habit scores and interference with QoL at each time-point; improvement in QoL assessed by IBS-QoL questionnaire.

Patients with score decrease higher than 75 points or rate decrease higher than 50% were evaluated in remission of the disease.

Adverse events were not registered during the administration of the composition of the invention and the composition resulted safety and well tolerated by all the patients.

At each time point, the absolute and relative change for the IBS-SS Total Score and each single items of IBS-SS were compared between treatment groups by a paired t-test and a mixed model for repeated measures, from baseline before the treatment.

The number of patients with an absolute IBS-Total Score lower than 75 points after 30 days at the end of treatment and the number of patients with a decrease of the relative change from baseline in the IBS-SSS abdominal pain higher than 50% at day 30 were compared between treatments by means of Chi-square test.

IBS-QoL Total Score and the eight domains have been summarized by treatment group after a treatment period of 30 days in respect to before the treatment. At the end of treatment the changes from baseline have been summarized by treatment group by means of descriptive statistics, and a paired t-test has been performed within each treatment group. Comparison between treatment groups on the IBS-QoL Total Score and the eight domains have been performed with an ANCOVA model with change from baseline as dependent variable, treatment as fixed effect and baseline value as covariate.

The patients treated with the composition of invention containing curcumin 42 mg and fennel oil 17.5 mg with curcumin daily dosage of 168 mg and fennel oil daily dosage of 70 mg showed a decrease of 50 points in respect to the placebo group in IBS-severity score.

Table 4 reports the IBS-SS total severity score with standard deviation for the groups treated with the composition of Example 1 (Group 1) and group treated with placebo composition (Group 2) during the treatment time in respect to the baseline.

TABLE 4

| | IBS-SS Total Severity score | | | |
|---|---|---|---|---|
| | 0 days | 10 days | 20 days | 30 days |
| Group 1 | 255.7 ± 39.9 | 198 ± 64.1 | 156.5 ± 68.3 | 127.8 ± 77.4 |
| Group 2 | 263.2 ± 34.4 | 228.3 ± 54 | 212.3 ± 75.5 | 195.5 ± 88.0 |

IBS-SS total severity score decreased in a significant mode in patient treated with the composition containing curcumin and fennel oil in respect to the placebo group.

Table 5 reports the percentage of patients which reported a reduction of IBS severity score more than 50 point and more than 75 point in respect to the placebo at the end of treatment.

TABLE 5

| | IBS-SS >50 points* | IBS-SS >75 points** |
|---|---|---|
| Group 1 | 81% | 25.9% |
| Group 2 | 50.8% | 6.8% |

[*P < 0.001; **P = 0.005]

The results have demonstrated the beneficial effect of the compositions containing curcumin and fennel oil in patients with functional gastrointestinal disorders.

Abdominal pain symptom was reduced in a percentage of patient treated with the composition of Example 1 in a percentage of 63.8% compared to 27% of patient treated with placebo.

At the end of treatment, the mean change from baseline of the IBS-QoL (total score) was significantly greater with the composition of Example 1 than placebo (17.4±19.2 vs. 7.7±18.0, ANCOVA P=0.03) with adjusted mean difference between treatments of 9.19 (95% CI of 3.13; 15.25). The treatment of IBS with composition of Example 1 was associated with a significant improvement in each of the 8 domains of IBS-QoL score (0.002<P<0.033). Table 6 reports the reduction in the features of the questionnaire in respect to the baseline. The adjusted mean are reported in the tables with their 95% confidence interval.

No adverse reaction was reported during the administration of the composition containing curcumin and fennel oil and it resulted well tolerated by the patients.

TABLE 6

| IBS-SS Symptom (absolute score) | Day 0 | | Day 10 | | Day 20 | | Day 30 | |
|---|---|---|---|---|---|---|---|---|
| | Group 1 | Group 2 | Group 1 | Group 2 | Group 1 | Group 2 | Group 1 | Group 2 |
| Abdominal distension | 52.7 ± 13.8 | 51.5 ± 16.5 | 38.3 ± 15.1 | 48.1 ± 18.3 | 30.9 ± 15.5 | 44.1 ± 21.7 | 25.3 ± 18.1 | 39.5 |
| Dissatisfaction with bowel habit | 56.2 ± 18.4 | 61.6 ± 18.5 | 47.5 ± 19.2 | 51 ± 19.9 | 40.8 ± 18.9 | 48.6 ± 18.9 | 36 ± 19.6 | 45.6 ± 21.7 |
| Interference with quality of life* | 58.0 ± 14.1 | 57.9 ± 16.8 | 47.7 ± 16.2 | 52.1 ± 18.0 | 39.9 ± 16.6 | 48.4 ± 19.7 | 32.0 ± 19.3 | 45.6 ± 21.5 |
| Days in the last 10 days with abdominal pain | 6 ± 1.8 | 5.8 ± 1.7 | 7.2 ± 2.2 | 6.6 ± 2.3 | 8 ± 2 | 7 ± 2.3 | 8.6 ± 1.6 | 7.2 ± 2.3 |

The invention claimed is:

1. A method of treating Irritable Bowel Syndrome (IBS) in a human in need thereof, said method comprising: orally administering to said human a nutritional composition consisting of curcumin in an amount from 10 to 200 mg and fennel essential oil in an amount from 5 to 50 mg together with pharmaceutical excipients, wherein the Irritable Bowel Syndrome total severity scores are between 100 and 300.

2. The method according to claim 1, wherein the nutritional composition consists of curcumin in an amount from 20 to 100 mg and the fennel essential oil is in an amount from 15 to 35 mg.

3. The method according to claim 1, wherein the nutritional composition consists of 42 mg curcumin, 600 mg polysorbate 80, 17.5 mg fennel essential oil and 3.5 mg citric acid in a gelatin capsule.

4. The method according to claim 1, wherein the nutritional composition is administered at curcumin daily dosage from 10 to 3200 mg and fennel oil from 5 to 800 mg.

5. The method according to claim 4, wherein the nutritional composition is administered at curcumin daily dosage from 20 to 1600 mg and fennel oil from 15 to 560 mg.

6. The method according to claim 4, wherein the nutritional composition is administered at curcumin daily dosage from 40 to 800 mg and fennel oil from 15 to 400 mg.

7. The method according to claim 1, wherein the nutritional composition is administered for a period of time of at least 10 days.

8. The method according to claim 7, wherein the nutritional composition is administered for a period of time between 10 and 30 days.

9. A method of preparing a nutritional composition consisting of curcumin in an amount from 10 to 200 mg and fennel essential oil in an amount from 5 to 50 mg together with pharmaceutical excipients, said method comprising the steps of:
   mixing curcumin with citric acid and polysorbate 80 and stirring until a homogenous mixture is formed;
   adding fennel essential oil under stirring and loading the formed homogenous mixture into a gelatin capsule;
   wherein the fennel essential oil is 2.5% by weight of the nutritional composition.

10. The method according to claim 1, wherein the nutritional composition is administered in functional food, aqueous solution, beverage, solid or semisolid food.

11. A kit system comprising a nutritional composition consisting of curcumin in an amount from 10 to 200 mg and fennel essential oil in an amount from 5 to 50 mg together with pharmaceutical excipients in the form of a gelatin capsule; wherein the fennel essential oil is 2.5% by weight of the nutritional composition.

* * * * *